US00PP15854P2

(12) United States Plant Patent
Woody

(10) Patent No.: US PP15,854 P2
(45) Date of Patent: Jul. 12, 2005

(54) EASTERN REDBUD TREE NAMED 'LITTLE WOODY'

(50) Latin Name: *Cercis canadensis*
Varietal Denomination: Little Woody

(76) Inventor: Paul Buddy Ewing Woody, 1821 Indian Trails, Morganton, NC (US) 28655

( * ) Notice: Subject to any disclaimer, the term of this patent is extended or adjusted under 35 U.S.C. 154(b) by 96 days.

(21) Appl. No.: 10/744,176

(22) Filed: Dec. 23, 2003

(51) Int. Cl.[7] ..... A01H 5/00
(52) U.S. Cl. ..... Plt./216
(58) Field of Search ..... Plt./216

*Primary Examiner*—Anne Marie Grunberg
*Assistant Examiner*—June Hwu
(74) *Attorney, Agent, or Firm*—Myers Bigel Sibley & Sajovec, P.A.

(57) ABSTRACT

A new and distinct ornamental cultivar of *Cercis canadensis* called 'Little Woody' is described that is a dwarf, vase-shaped tree with small, green, heart-shaped leaves.

2 Drawing Sheets

Latin name of the genus and species: The Latin name of the novel cultivar disclosed herein is *Cercis canadensis* L. (Leguminosae Juss.).

Variety denomination: The inventive cultivar of eastern redbud tree disclosed herein has been given the cultivar denomination 'Little Woody'.

BACKGROUND OF THE INVENTION

The redbud tree, *Cercis canadensis*, sometimes referred to as the Judas tree because it dates back to biblical times, is a small deciduous tree that displays an abundance of purple blossoms in the spring. It has large heart-shaped leaves during the summer, and may have long seedpods and yellow leaves in the fall. Redbud trees are generally used for ornamental purposes.

The inventive cultivar named 'Little Woody' was discovered in a cultivated area of 300–400 *Cercis canadensis* L. (Leguminosae Juss.) seedlings planted in 1997. When planted, the seedlings ranged in size from 18–24 inches (45–60 cm) in height and grew to 8–10 feet (~3 meters) by the year 2000. 'Little Woody' was selected in 2000 for its distinctive dwarf habit, vase shape, and small leaves. While other redbud trees generally require some selective pruning to obtain a desirable shape, 'Little Woody' requires no pruning to maintain its vase shape.

SUMMARY OF THE INVENTION

'Little Woody' is a new and distinct cultivar of eastern redbud tree characterized by its dwarf habit, vase shape, and small leaves. Like *C. canadensis* subsp. *mexicana* (Rose) Murray, 'Little Woody' has small leaves; however, 'Little Woody' is distinctive by lacking the wavy margins and shiny surface characteristic of *C. canadensis* subsp. *mexicana* (Rose) Murray. Further, 'Little Woody' has smaller leaves than either *C. canadensis* subsp. *texensis* or *C. canadensis* subsp. *canadensis*. Moreover, 'Little Woody' has green leaves, unlike the intense red-purple leaves of the well-known cultivar 'Forest Pansy' (unpatented) and lacks the weeping growth form of 'Covey' (U.S. Plant Pat. No. 10,328) and 'Traveller' (U.S. Plant Pat. No. 8,640).

BRIEF DESCRIPTION OF THE DRAWINGS

The accompanying photographs were taken of a typical seven-year old plant of 'Little Woody'.

DETAILED BOTANICAL DESCRIPTION OF THE VARIETY

The following is a detailed botanical description of a new and distinct cultivar of *Cercis canadensis* known as 'Little Woody'. Plant growth observations were of mature plants (approximately seven-years old) grown in full sun in field plots (soil pH of 6.5) in Burke County, N.C. in late winter, spring and summer of 2003 (March: observations of deciduous form, buds; April: observations of inflorescences and flowers before leaves emerged; July: observations of mature vegetative growth). Where dimensions, sizes, colors and other characteristics are given, it is to be understood that such characteristics are set forth as accurately as practicable. Those skilled in the art will appreciate that certain characteristics will vary with older or, conversely, with younger plants. 'Little Woody' has not been observed under all possible environmental conditions. The phenotype of the cultivar may differ from the descriptions herein with variations in the environment such as season, temperature, light intensity, day length, cultural conditions, and the like. Color notations are based on The Royal Horticultural Society Colour Chart, The Royal Horticultural Society, London, 1995 edition.

Market Class

The market class of the cultivar is ornamental tree.

Parentage

The 'Little Woody' cultivar was selected from a cultivated mass planting of *Cercis canadensis* L. (Leguminosae Juss.)

at Morganton, N.C. The single, individual plant now known as 'Little Woody' was selected in 2000 because of its multitude of exceptional features, and has been propagated asexually since that time.

Asexual Reproduction

In August 2000, 'Little Woody' was propagated asexually by budding to produce two, second-generation plants at Shadow Nursery located in Winchester, Tenn. to increase the plant population and evaluate the stability and uniformity of the distinctive characteristics over several generations. Since that time, 'Little Woody' has been asexually reproduced at the Shadow Nursery predominantly by budding of seedlings. Budding in August 2001 generated approximately 50, third-generation plants, and approximately 150 plants were produced in an August 2002 fourth generation. Asexual propagation of the new cultivar has shown that the unique features of this new eastern redbud are stable and the plant reproduces true to type in successive cycles of asexual propagation.

Technical Description of the Variety

Figure 1:
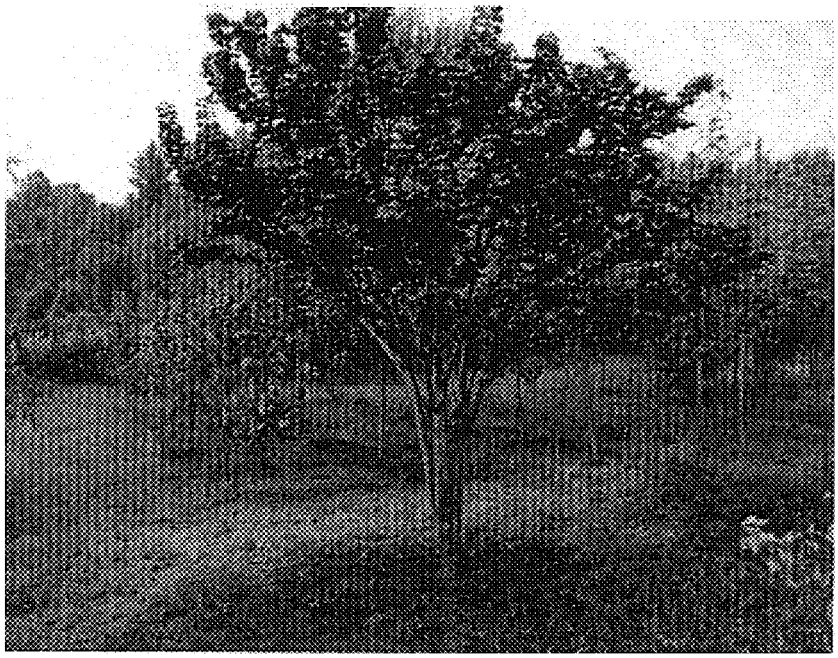
FIG. 1 shows a typical plant of 'Little Woody' in the summer.

Plant habit: 'Little Woody' has an average height of 10 feet (~3.3 meters) and an average spread of 8 feet (~3 meters). This cultivar is vase-shaped with an ascending-spreading crown providing a filtered sunlight canopy (FIG. 1).

*Trunk dimensions and appearance.*—'Little Woody' has one trunk averaging ~10 cm in diameter and ~30 cm in height. The trunk has grayish bark (RHS 197A), splitting longitudinally to form ridges ~3–8 mm wide. The indentations are ~1–3 mm wide and ~1–1.5 mm deep.

*Branches from trunk.*—In general, nine branches emerge from the trunk and are strongly ascending, divergent and 3–6 cm in diameter. The bark of mature branches is grayish (RHS 201A) in color.

*Crown major branches.*—Spreading-ascending, pins forming conspicuous herringbone pattern; pins spreading to suberect, forming narrow to broad V-shaped pattern along branch.

*Young branches.*—Slender, 3–6 mm diameter, dark gray-brown to brown; bark becoming striated; lenticels prominent, weakly raised, circular to slightly angled; inner wood is whitish, pith is solid. The bark of immature branches is grayish-green (RHS 147B) and the branches become grayer with age (RHS 146A).

*Lenticels.*—Numerous, orbicular to weakly oval in shape with length slightly longer than width. ~0.1–0.4 mm in diameter and yellowish-green (RHS 152D) in color.

Figure 2:
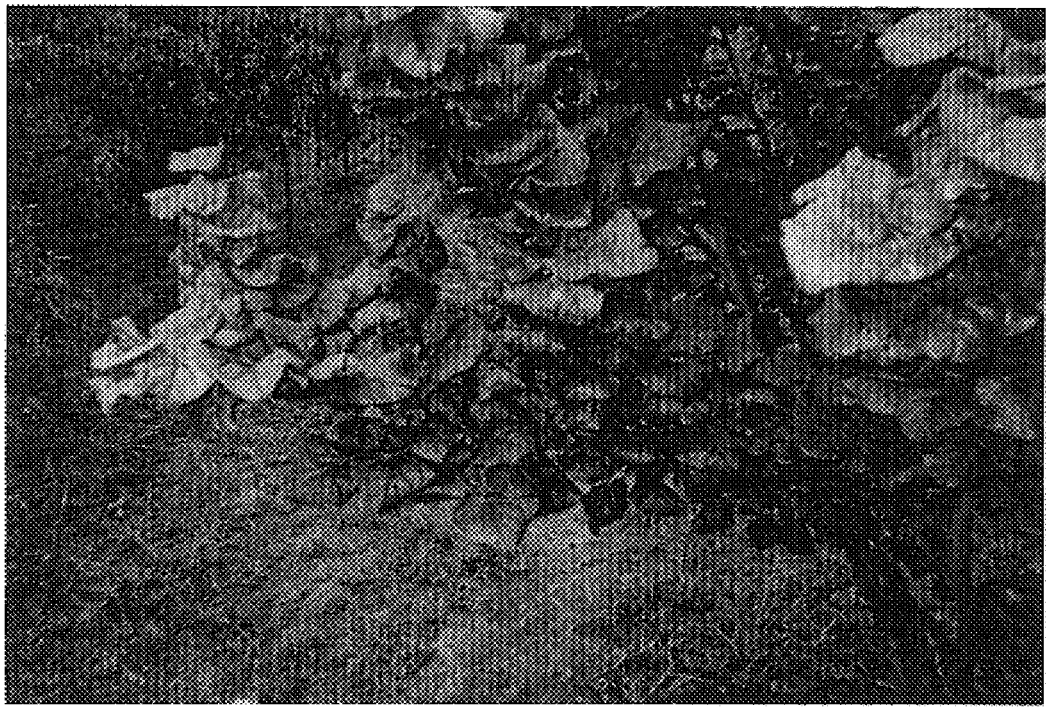
FIG. 2 shows leaves typical of 'Little Woody'.

Foliage: Deciduous leaves are alternate, simple, broad, and ovate-cordate. In general, the leaves are (3) 4–6 cm in length and 4–7 cm in width (FIG. 2). Margin: entire and slightly turned downward; apex: broad acute, mucronate; base: cordate lobes 15–25 mm long below petiole insertion, 10–15 mm wide between lobe bases; adaxial (upper) surface: dark green (RHS 132A), bullate-rugose; abaxial (lower) surface: pale-grayish green (RHS 191A), primary veins seven, palmate, veinlets conspicuously reticulate below with the naked eye, prominent at 7X magnification.

*Petioles.*—Slender, smooth, 2–2.6 cm long and 2.3–2.6 mm in diameter, bearing a pulvinus distally; yellowish-green, ranging between and including RHS 144B and RHS 145A (depending on exposure to sun, which results in a darker color); becoming reddish-tinged on adaxial surface when exposed to sun (RHS 178B).

*Pulvinus.*—Apically on the petiole, 2–3 mm long.

Buds: Swelling in late March, reddish-purple (RHS 58A) in clusters of (3) 4–8. Buds are erect, inverted conical, ~2–3 mm long and 1–1.5 mm wide basally expanding to 2.5–3.5 mm apically. Bracts are scale-like, appressed, imbricate, flabellate, obtuse, ciliolate, and ~0.7–1.0 mm long and 1.0–1.5 mm wide.

*Pedicels.*—Less than ~1 mm in length.

*Calyx.*—Narrow campanulate; tube: ~1 mm long, ~1.5 mm wide; teeth: broad ovate, obtuse, ~0.5 mm long, 0.4–0.6 mm wide.

Figure 3:
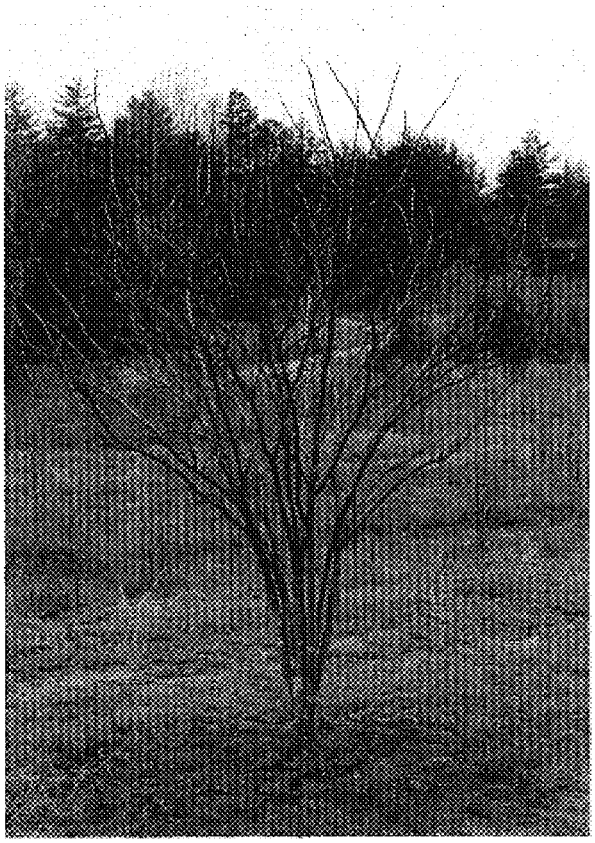
FIG. 3 shows a typical plant of 'Little Woody' in the spring.

Inflorescence: Abundant, cauliflorous on old wood before leaves appear, bearing cluster of 2–7 flowers in early April (FIG. 3).

*Bracts.*—Imbricate, becoming larger distally, broad ovate, obtuse, ciliolate, largest ~1.0–1.5 mm long, 1.5–2.0 mm wide.

*Pedicels.*—4–5 mm long in flower.

Figure 4:
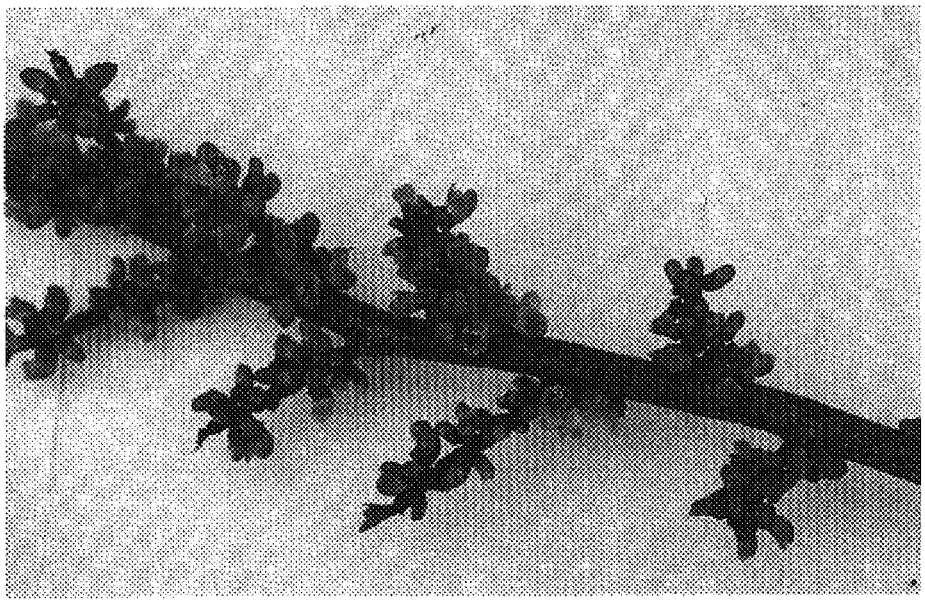
FIG. 4 shows flowers produced by 'Little Woody'.

Flowers: Papilionaceous (pea-like), pedicillate, purplish (RHS 81B–C) (FIG. 4).

*Calyx.*—Broad campanulate, red-purple (RHS 71B–C); tube: 10-veined, ~1 mm long, 2.5–3 mm wide; lobes: ovate, obtuse, 1–2 mm long, 1–1.5 mm wide, shriveling upon maturation.

*Petals.*—Five, papilionaceous, claws lacking pigmentation; two keel petals, enclosing reproductive organs, blade obtuse ~5 mm long, 3–3.5 mm wide, claw ~2 mm; two wing petals, ascending, blade oblong, obtuse, ~4 mm long, 2.5–3 mm wide, claw 2.5–3 mm; one banner petal, ~4 mm long, ~3 mm wide, claw ~2 mm.

*Stamens.*—Ten, distinct, free; filaments: 4–4.5 mm long; anthers: ~0.7 mm.

*Pistil.*—One, exceeding stamens slightly; ovary: ~3.5 mm long; style: 2.5–3.0 mm long, curving some apically; stigma: capitate, ~0.3 mm diameter.

Fruit: Fruit is rarely produced.

Hardiness: 'Little Woody' is hardy, surviving temperatures below −3° C. The cultivar has performed well under extreme environmental conditions including cold, snow, ice storm, drought and heavy rains.

Plant disease: None observed.

Pest resistance/susceptibility: Slight infestation of Japanese beetles observed; infestation controlled by spraying or picking off caterpillars.

Comparison with other *Cercis canadensis* Subspecies and Cultivars

'Little Woody' is distinctive from the three subspecies of *Cercis canadensis,* (i.e., *canadensis, mexicana,* and *texenis*) which are distinguished primarily by native population ranges. *C. canadensis* supsp. *mexicana* (Rose) Murray is characterized as having small, shiny leaves with wavy margins (Dirr (1998) In: Manual of Woody Landscape Plants, $5^{th}$ Edition, Stipes Publishing Co., Champaign, Ill., pp 208–211), whereas 'Little Woody' has a similar leaf size but lacks wavy margins and a shiny appearance. Of five herbarium species of *C. canadensis* supsp. *mexicana* located at the North Carolina State University Herbarium, two specimens (Russell 2184 and 2191) are similar in size to 'Little Woody' and the remaining three (Russell 2170, 2171 and 2183) have leaves that are larger than 'Little Woody'. In addition, the leaves of 'Little Woody' are slightly thicker and bullate-rugose with margins slightly turning downward. Subspecies *canadensis* and *texenis* have larger leaves than 'Little Woody', however, subspecies variation has been noted (Dirr (1998) supra).

In a comparison with known cultivars of *C. canadensis,* the leaves of 'Little Woody' are green and lack the intense reddish-purple pigmentation and subdued reddish-purple hue common to 'Forest Pansy' in emerging and older leaves, respectively. Further, 'Covey' and 'Traveller' are dwarf in stature (up to 2 meters in height) and have arching-recurving branches which produce a weeping growth form, whereas 'Little Woody' has a vase-shaped canopy.

Herbarium Vouchers

Herbarium vouchers will be deposited upon patenting at North Carolina State University Herbarium, Raleigh, N.C. and The National Arboretum, Washington, D.C. with Holotype: Fantz & Woody 7402 (foliage) and Paratypes: Fantz & Woody 7291 (flowers) and Fantz & Woody 7266 (buds).

What is claimed is:

1. A new and distinct cultivar of *Cercis canadensis* plant named 'Little Woody', substantially as illustrated and described herein.

* * * * *